United States Patent [19]

Salloum et al.

[11] Patent Number: 5,030,658

[45] Date of Patent: Jul. 9, 1991

[54] ENHANCED ACTIVITY ARTHROPODICIDAL SOLUTION

[75] Inventors: Greg Salloum, Victoria; George Puritch, Saanichton; Michelle Gorman, Victoria; Roderick Bradbury, Sidney, all of Canada

[73] Assignee: Safer, Inc., Newton, Mass.

[21] Appl. No.: 438,748

[22] Filed: Nov. 17, 1989

Related U.S. Application Data

[62] Division of Ser. No. 190,146, May 4, 1988, abandoned.

[51] Int. Cl.$^5$ ............... A01H 37/00; A01H 37/12; A61K 31/19; A61K 31/20
[52] U.S. Cl. ........................... 514/560; 514/557; 514/563; 514/566
[58] Field of Search ............ 514/25, 560, 941, 975, 514/738; 424/DIG. 6

[56] References Cited

U.S. PATENT DOCUMENTS

| | | | |
|---|---|---|---|
| 2,735,742 | 2/1956 | Godehen | 8/137.5 |
| 2,755,304 | 7/1956 | Bersworth et al. | 564/506 |
| 4,324,797 | 4/1982 | Suzuki | 424/287 |

OTHER PUBLICATIONS

Puritch; Proceedings of the 23rd Annual Lower Mainland Horticulural Improvement Association Growers' Short Course Feb., 11, 12 & 13, 1981, Abbotsford, B.C.

*Primary Examiner*—Frederick E. Waddell
*Assistant Examiner*—Theodore J. Criares
*Attorney, Agent, or Firm*—Lahive & Cockfield

[57] ABSTRACT

Disclosed are arthropodicidal solutions for application to plants comprising, as an active ingredient, arthropodicidally active mono alpha carboxylic acids, of hydrocarbons having 8 to 20 carbon atoms, and/or monovalent metal salts thereof. The arthropodicidal activity of these fatty acids is potentiated by including in the solution an agent capable of sequestering metal ions such as one or a mixture of chelateing agents, sequestering agents, and surfactants.

8 Claims, No Drawings

ENHANCED ACTIVITY ARTHROPODICIDAL SOLUTION

This application is a division of U.S. application Ser. No. 190,146, filed May 4, 1988, abandoned.

BACKGROUND OF THE INVENTION

This invention relates to arthropodicidal solutions and more particularly to aqueous solutions effective in controlling phytophagous insects and arachnids characterized by enhanced arthropodicidal effectiveness and improved environmental compatability.

The use of insecticides has greatly enhanced agricultural productivity, but it has become apparent that there are limits to the amount of petrochemical based materials that safely can be absorbed into the environment. Catastrophic, unanticipated, relatively long term effects experienced with materials such as DDT have increased awareness of the potentially dangerous environmental impact of widespread use of synthetics, contributed to the creation of regulatory agencies charged with protecting the environment, and promoted the development of potent, but apparently less dangerous insecticidal materials made from petrochemicals. These new insecticides are nevertheless far from ideal from the point of view of environmental safety, and sometimes collect in food and fresh water resources.

Salts of fatty acids, primarily sodium or potassium fatty acid soaps, recently have been used as an insecticide. Compositions having excellent insecticidal properties which exploit these salts are available commercially under the trademark SAFER INSECTICIDAL SOAP. These fatty acid soaps are naturally occurring materials having no known long-term environmental effects. They are effective against mites and soft bodied insects such as aphids and whiteflies, but less effective against other types of arthropods.

While the mode of activity of monovalent metal salts of monocarboxylic fatty acids has not been elucidated, it is apparent that this type of active compound must be dissolved in water in order to exhibit its arthropodicidal activity. When concentrates of SAFER INSECTICIDAL SOAP are diluted with hard water, i.e., water containing significant quantities of calcium and/or magnesium ions, the monocarboxylic acid anions tend to precipitate leading to reduced arthropodicidal activity.

It is an object of this invention to provide an arthropodicidally active solution of monovalent metal salts of fatty acids which have potentiated arthropodicidal activity and which can be diluted with water from various sources, having various concentrations of hardness ions, without reducing the arthropodicidal activity of the solution per unit weight of active salt. Another object is to provide a method of protecting plants from phytophagous arthropods comprising applying to the plant a potentiated solution of monocarboxylic fatty acids or their monovalent metal salts.

These and other objects of the invention will be apparent from the following.

SUMMARY OF THE INVENTION

It has now been discovered that known chemical agents capable of sequestering metal ions can act as potentiators or synergists for arthropodicidally active aqueous solutions of monocarboxylic fatty acids and their monovalent metal salts. The enhanced activity has been observed with a wide variety of known chemical agents useful for sequestering metal ions, including various chelating agents, other substances which complex metal ions or otherwise mask the chemical activity of such ions in other than classical polydentate chelate structures, and surface active agents capable of sequestering metal ions in solution by micelle formation or otherwise.

Broadly, the invention comprises a method of protecting a plant from phytophagous arthropod infestation, e.g., from damage caused by sucking or chewing hard or soft bodied insects, and a composition used by direct application to the plant and the infesting arthropods by, for example, conventional spray application. The composition comprises an aqueous solution of an arthropodicidally effective amount of a composition comprising an arthropodicidally active monocarboxylic fatty acid and/or its monovalent metal salt and a sequestering agent for metal ions present together with the active components in solution in an amount sufficient to increase the arthropodicidal effect of the fatty acid active ingredients. Preferably, the active ingredient comprises a mixture of monovalent metal salts, e.g., potassium or sodium salts, of fatty acids having eight to twenty carbon atoms. Monocarboxylic acid salts having eight to twelve carbon atoms work well. Most preferably, the fatty acid salt component of the solution is rich in unsaturated fatty acid salts having eighteen carbon atoms in the hydrocarbon chain, e.g., contains a substantial content of oleic and linoleic acid esters. The potentiating effect has been observed both with active salts and active acids. The active ingredients are referred to collectively herein as fatty acid salts.

Broadly, the nature of the sequestering agent used in the potentiated composition determines the optimal concentration of sequestering agent in a given preparation. Generally, the ratio of fatty acid salts to sequestering agent, on a weight basis, can vary between 1:0.05 to 1:5, but usually the agent is present in amounts no greater than the fatty acid salt content. Ratios outside these ranges may be used, but result generally in barely significant improvement at the lower amounts of sequestering agent or reagent waste at the higher amounts. Useful sequestering agents include chelating agents, for example, organic nitrogen-containing and/or carboxylic acid-containing chelating agents, hard water ion complexing agents, particularly those comprising phosphate groups such as water-soluble phosphate salts, pyrophosphates, and tripolyphosphates, and dispersing agents having a high affinity for hard water ions, preferably anionic or nonionic dispersing agents.

While the reasons why such sequestering agents have the ability to increase toxicity of fatty acid salts to arthropods is unknown, it is clear that the observed effect is not simply a matter of preventing formation of lime soap and resulting precipitation in the presence of hardness ions because the enhanced effect is observed in both hard and soft waters, including deionized water.

The foregoing and other features of the invention will be apparent from the description and claims which follow.

DETAILED DESCRIPTION

The arthropodicide of the invention employs an arthropodicide comprising monocarboxylic fatty acid monovalent metal salts or acids and a metal ion sequestering agent. Either one, or preferably, a mixture of fatty acid salts are normally employed. Preferred fatty acid salts are those having between eight and twenty carbon atoms in a straight chain structure with the alpha carbon comprising a monocarboxylic acid moiety esterified, preferably completely, with a monovalent metal such as sodium or potassium. This group of fatty acids are known to have insecticidal activity, and have been used for many years in the control of pestiferous arthropods. These materials are widely commercially available. They are produced from coconut oils, comprising predominantly a mixture of laurate (C-12) and myristate (C-14). They are also derived from various plant and animal sources. The preferred fatty acids are those having eight to eighteen carbon atoms including caprylate and stearate. Most preferred are unsaturated, eighteen carbon atom salts such as alkali metal oleate and linoleate, and saturated eight to twelve carbon atom salts such as mixtures of alkali metal caprylate, pelargonate, caprate, undecylinate and laurate.

A preferred composition comprises the fatty acid salt component of solutions available from Safer, Inc. of Newton, Mass. under the trademarks SAFER INSECTICIDAL SOAP. The composition of this product varies slightly from batch to batch, but always includes at least about 35% salt, or acid form, oleic acid, and at least about 6% salt, or acid form, linoleic acid. The remainder of the solutes comprise other fatty acids or salts having between 12 and 20 carbon atoms. The soap component is present in the commercial concentrate at levels in the range of 50% by weight.

When a metal ion sequestering agent is added to these aqueous mixtures of fatty acid salts, they exhibit an unanticipated increase in mortality of pestiferous arthropods. The enhanced toxicity is evident even when the absolute concentration and relative amounts of active ingredients are varied. Optimal composition is dependent on the arthropod target species, the stage of arthropod growth, and anticipated temperature at application. Concentration ratios and absolute concentrations of ingredients of specific compositions readily can be optimized empirically. Some species of sequestering agents have been observed to be very mildly toxic to phytophagous arthropods. However, generally, even sequestering agents which are not themselves toxic to arthropods to any significant extent nevertheless may be used in accordance with the invention. In those instances where a sequestering agent intended for use in an experimental composition has been found to have some toxicity, the toxicity of the composition has been greater than the sum of the toxicities of the individual ingredients in all cases tested to date.

The result-effective chemical property of the sequestering agents useful in the composition of the invention appears to be their ability to reduce the chemical activity of metal ions, and particularly divalent metal ions. This is a known property of many chelating agents and sequestering agents. It also is a property of strong anionic, as well as some non-ionic and amphoteric surface active agents. In general, any composition useful in significantly "softening" water may be used in admixture with the fatty acid salts to improve their arthropodicidal activity.

Among the chelating agents which may be used are carboxylic acid chelating agents such as citrate, gluconate, and ascorbate, and alkylenepolyamine polyacetic acids such as nitrilotriacetic acid, N-2-hydroxyethylaminodiacetic acid, ethylenediamine tetraacetic acid (EDTA), diethylene triamine penta acetic acid, N-2-hydroxyethyl ethylenediamine triacetic acid, propylene-1, 2-diamine tetracetic acid, propylene-1, 3-diamine tetracetic acid, and the isomeric butylenediamine tetraacetic acids. Either an alkali metal salt or alkanolamine salt of these chelating agents may be used.

Another class of sequestering agents useful in the composition of the invention are water-soluble phosphate-containing sequestering agents such as tripolyphosphates and phosphate salts. Excellent results have been observed using $NH_4H_2PO_4$.

Another class of agents which are capable of sequestering metal ions and may be used in compositions of the invention are anionic surfactants such as alkali metal or ammonium salts of lauryl alkanolamide sulphosuccinate, alkylarylpolyether sulphates and sulfonates, cocoisethionate and lignosulphonates. Also useful are amphoteric surfactants such as the water soluble salts of coco-betaine, coco-amphocarboxlyglycinate, coco-sulphobetaine, and imidazoline. Non-ionic surfactants such as alkylphenolethoxylate, and compounds known to be useful to sequester hard metal ions such as alkylphenolethoxylated phosphate, citrate, or fatty acid esters. Of course, compatible mixtures and blends of any of the foregoing may also be used. In summary, there is a wide variety of commercially available sequestering agents which may be used to formulate insecticidal compositions embodying the invention.

In addition to the foregoing, minor amounts of non-insecticidally active fatty acids and other ingredients such as alcohol, may be included to function as carriers, solvation aids, adjuvants, emulsifiers, spreaders, stabilizers, preservatives, etc.

The compositions may be manufactured simply by mixing the ingredients together in water. Preferably, the compositions are supplied to the trade as a concentrate which is diluted, either with hard or soft water, and applied directly to the leaves and fruit of plants and the arthropods present thereon as a spray using conventional spraying equipment. A preferred ready-to-use solution has a fatty acid salt concentration on the order of 1% by weight.

The fatty acid salt component of the composition comprise naturally occurring substances which have no known long-term environmental effects. Sequestering agent are ubiquitous in commerce. Many are approved as food additives, and the environmental effect of their use in insecticidal compositions is minimal. Accordingly, the composition provides an effective arthropodicide useful in controlling plant damage caused by phytophagous insect and other arthropod species which is environmentally preferred over petrochemical based insecticides currently used in agriculture and horticulture. The composition is appropriate for use in enclosed environments such as living space and greenhouses.

Because of the potentiating effect of the chelating or sequestering agent, the amount of fatty acid salts required to obtain a given level of insect kill is substantially reduced. Since fatty acid salts can be phytotoxic when used at higher concentration, the addition of the potentiating agent to such compositions provides a more economical and less phytotoxic solution permitting use of lower concentrations of active ingredients.

In the examples which follow, all of the compositions were made by mixing together in soft or deionized water (excepting where use of hard water is specifically set forth) a potentiating agent and a fatty acid salt or mixture in the various absolute concentrations and weight ratios indicated. In each test, statistically significant data were collected on the effects of compositions embodying the invention, and on the various individual components used separately, on various target species, using established, controlled, testing procedures. The examples illustrate the invention but should not be regarded as limiting.

EXAMPLE 1

The effectiveness of various compositions embodying the invention was tested together with SAFER INSECTICIDAL SOAP (SIS) at various levels on two spotted spider mites. The tests were conducted by spraying the soap alone, the chelating agent alone, and then a mixture of the two for each test run. Percent kill was assessed for the components of the composition used individually, and these were added together to obtain the expected mortality. The data are set forth in Table 1 below.

TABLE 1

| Ingredient (weight %) | % Mortality Observed | % Mortality Expected |
| --- | --- | --- |
| A. SIS (0.05) | 16.2 | |
| Na gluconate (0.075) | 2.2 | |
| mix | 50.2 | 18.4 |
| B. SIS (0.05) | 8.6 | |
| Na gluconate (0.12) | 0 | |
| mix | 92.2 | 8.6 |
| C. SIS (0.05) | 8.6 | |
| Na gluconate (0.15) | 0 | |
| mix | 100 | 8.6 |
| D. SIS (0.05) | 2.5, 6.3 | |
| ascorbic acid (0.15) | 0, 5 | |
| mix | 83.8, 72.5 | 2.5, 11.3 |
| E. SIS (0.05) | 21.4 | |
| $Na_4$ EDTA (0.12) | 4.3 | |
| mix | 82.9 | 25.7 |
| F. SIS (0.05) | 25.7 | |
| $Na_2$ EDTA (0.15) | 2.9 | |
| mix | 88.7 | 28.6 |
| G. SIS (0.05) | 3.8 | |
| Cheelox B-13[1] (0.15) | 2.5 | |
| mix | 63.8 | 6.3 |
| H. SIS (0.2) | 32.8 | |
| $Na_4$ EDTA (0.12) | 1.4 | |
| mix | 84.3 | 34.2 |
| I. SIS (0.05) | 10 | |
| Na tripolyphosphate (0.12) | 1 | |
| mix | 64 | 11 |
| J. 1000 ppm hard water | 1.3 | |
| $NH_4H_2PO_4$ (0.12) in 500 ppm hard water | 3.8 | |
| $NH_4H_2PO_4$ (0.12) in 1000 ppm hard water | 3.8 | |
| SIS (0.4) in 500 ppm hard water | 17.5 | |
| SIS (0.4) in 1000 ppm hard water | 11.3 | |
| mix in 500 ppm hard water | 90.0 | 21.3 |
| mix in 1000 ppm hard water | 88.8 | 15.1 |

[1] mixed sodium and alkanolamine salt of alkyldiamine polyacetic acid - G.A.F. corp.

As illustrated by the data, the presence of a chelating or sequestering agent uniformly increases the percent mortality of the fatty acid salts over that which could be expected based on the additive effects of the salt plus the sequestering agent. Furthermore, the effect is observed in hard water as well as tap water having a very low hardness ion content.

EXAMPLE 2

Pesticidal potassium salts of fatty acids obtained commercially and derived from botanical and animal sources rich in saturated and unsaturated eighteen carbon monocarboxylic fatty acids (K salts) were mixed with tetrasodium ethylenediamine tetracidic acid (EDTA) in a ratio of fatty acid salt to chelator ranging from 1:0.25 to 1:1. The percent mortality induced by the individual components and by the mix was assessed in a standard test on cabbage loopers. The results are set forth in Table 2.

TABLE 2

| Ingredient (% by weight) | % Mortality observed | % Mortality Expected |
| --- | --- | --- |
| K salts (0.2) | 37.5 | |
| EDTA (0.05) | 25 | |
| EDTA (0.1) | 10 | |
| EDTA (0.2) | 27.5 | |
| K salt (0.2) + EDTA (0.05) | 82.5 | 62.5 |
| K salt (0.2) + EDTA (0.1) | 77.5 | 47.5 |
| K salt (0.2) + EDTA (0.2) | 85.0 | 65.0 |

As is evident from the data, compositions ranging in fatty acid to sequestering agent ratio from 1:0.25 to 1:1 uniformly exhibit enhanced activity greater than could be expected from the additive effect of the sequestering agent and potassium fatty acid salts alone.

EXAMPLE 3

In this example, potassium salts of coconut oil fatty acids (approximately 45% C-12, lesser amounts of C-14, unsaturated C-18, and other fatty acids) are mixed with sodium gluconate at a 1:1.5 ratio of salt to sequestering agent and sprayed on cabbage aphids. The percent mortalities observed when the spray contained the components individually and in admixture at two different absolute concentrations (1:1.5 ratio) are set forth in Table 3 below.

TABLE 3

| Ingredient (% by weight) | % Mortality observed | % Mortality Expected |
| --- | --- | --- |
| K salt (0.2) | 13 | |
| K salt (0.4) | 26 | |
| Na gluconate (0.3) | 8 | |
| Na gluconate (0.6) | 9 | |
| K salt (0.2) + Na gluconate (0.3) | 45 | 21 |
| K salt (0.4) + Na gluconate (0.6) | 78 | 35 |

This example again demonstrates the ability of sequestering agents to enhance insecticidal activity of fatty acid salts.

EXAMPLE 4

Lime soap dispersing agents useful in water softening applications also behave as potentiating agents. Several commerically available anionic and nonionic surfactant materials having insignificant anthropodicidal activity alone were tested in admixture with SIS in both hard and deionized water in controlled experiments on cabbage aphids and mites. Results are set forth below.

| Ingredients (percent by weight) | Percent Mortality |
| --- | --- |
| Cabbage Aphids in Distilled Water | |
| SIS (0.4%) | 73 |
| SIS (0.4%) Agriwet T-F[1] (0.1%) | 89 |
| SIS (0.4%) Stepfac 8170[2] (0.1%) | 93 |
| SIS (0.4%) Fenopon Co436[3] (0.1%) | 94 |
| SIS (0.4%) Fenopon TN-74[4] (0.1%) | 93 |
| Mites in 1000 ppm Hard Water | |

-continued

| Ingredients (percent by weight) | Percent Mortality |
|---|---|
| SIS (0.4%) | 4 |
| Stepfac 8173[5] (0.06%) | 31 |
| Mix | 63 |

[1] sodium N-methyl-N-oleoyl taurate (anionic)
[2] phosphate ester of alkyl phenoxy poly ethoxy ethanol (nonionic)
[3] ammonium salt of sulfated nonyl phenoxy poly (ethyleneoxy) ethanol (anionic)
[4] sodium-N-methyl-N-palmitoyl taurate (anionic)
[5] phosphate ester of alkyl phenol polyethoxy ethanol (nonionic)

EXAMPLE 5

In this experiment, oleic acid alone and in admixture with gluconic acid were assessed alone and together for anthropodicidal activity on two-spotted spider mites. The results are set forth in below.

| Ingredient (% by weight) | Percent Mortality Observed | Percent Mortality Expected |
|---|---|---|
| Oleic acid (0.05%) | 16 | |
| Oleic acid (0.2%) | 60 | |
| Gluconic acid (0.15%) | 3 | |
| Oleic acid (0.05%) + Gluconic acid (0.15%) | 99 | 19 |
| Oleic acid (0.2%) + Gluconic acid (0.15%) | 95 | 63 |

The invention may be embodied in other specific forms.

What is claimed is:

1. A method of protecting a plant from phytophagous arthropods comprising
   applying to the plant and anthropods thereon an aqueous solution of an anthropodically-effective amount of a composition comprising
   an anthropodically-active ingredient comprising the sodium or potassium salt of a mixture of monocarboxylic fatty acids having at least about 35% by weight of a salt of oleic acid, at least about 6% by weight of a salt of linoleic acid and the balance of salts of fatty acids having between 12 and 20 carbon atoms, and
   a chelating agent selected from the group consisting of the alkali metal salts or alkanolamine salts of carboxylic acids and alkylenepolyamine polyacetic acids, said agent being present in said solution in an amount sufficient to increase the anthropodicial effect of said active ingredient such that the ratio of said active ingredient to said agent is in the range of about 1:0.05 to about 1:5.

2. The method of claim 1 wherein the weight ratio in said solution of said active ingredient to said agent is within the range of 1:0.05 to 1:1.

3. An aqueous anthropodicidal solution comprising
   the sodium or potassium salts of a mixture of anthropodically active monocarboxylic fatty acids having at least 35% by weight of a salt of oleic acid, at least about 6% by weight of a salt of linoleic acid and the balance of salts of fatty acids having between 12 and 20 carbon atoms, and
   a chelating agent selected from the group consisting of the alkali metal salts or alkanolamine salts of carboxylic acids and alkylenepolyamine polyacidic acids, said agent being present in said solutions in an amount sufficient to increase the anthropodicidal effect of said active ingredient such that the ratio of said active ingredient to said agent is in the range of about 1:0.05 to about 1:5.

4. The solution of claim 3 wherein the weight ratio therein of said active ingredient to said agent is within the range of 1:0.05 to 1:1.

5. The method of claim 1 wherein said carboxylic acid ohelating agents are selected from the group consisting of alkali metal salts or alkanolamines salts of citrate, gluconate and ascorbate.

6. The method of claim 1 wherein said alkylenepolyamine polyacetic acid chelating agents are selected from the group consisting of the alkali metal salts or alkanolomine salts of nitrilotriacetic acid; N-2-hydroxyethylamidodiacetic acid; ethylenediamine tetracetic acid; diethylene triamine penta acetic acid; N-2-hydroxyethyl ethylenediamine triacetic acid; propylene-1, 2-diamine tetracetic acid; propylene-1, 3-diamine tetracetic acid; and isomeric butylenediaminetetracetic acids.

7. The composition of claim 3 wherein said carboxylic acid chelating agents are selected from the group consisting of alkali metal salts or alkanolamine salts of citrate, gluconate and ascorbate.

8. The composition of claim 3 wherein said alkylenepolyamine polyacetic acid chelating agents are selected from the group consisting of the alkali metal salts or alkanolamine salts of nitrilotriacetic acid; N-2-hydroxyethylamidodiacetic acid; ethylenediamine tetracetic acid; diethylene triamine penta acetic acid; N-2-hydroxyethylenediamine triacetic acid; propylene-1, 2-diamine tetracetic acid; propylene-1, 3-diamine tetracetic acid; and isomeric butylenediaminetetracetic acids.

* * * * *